United States Patent [19]

Kingston et al.

[11] Patent Number: 5,322,801
[45] Date of Patent: Jun. 21, 1994

[54] PROTEIN PARTNER SCREENING ASSAYS AND USES THEREOF

[75] Inventors: Robert E. Kingston; Christopher A. Bunker, both of Arlington, Mass.

[73] Assignee: The General Hospital Corporation, Charlestown, Mass.

[21] Appl. No.: 960,981

[22] Filed: Oct. 14, 1992

Related U.S. Application Data

[63] Continuation-in-part of Ser. No. 915,745, Jul. 21, 1992, abandoned, which is a continuation of Ser. No. 815,880, Jan. 7, 1992, abandoned, which is a continuation of Ser. No. 510,254, Apr. 19, 1990, abandoned.

[51] Int. Cl.$^5$ .................. C12N 15/09; C12N 15/62
[52] U.S. Cl. .................... 436/5.01; 435/69.7; 435/172.7; 536/23.4
[58] Field of Search ............ 436/501; 435/69.7, 172.3; 653/23.4

[56] References Cited

FOREIGN PATENT DOCUMENTS

| | | | |
|---|---|---|---|
| WO89/07654 | 8/1989 | PCT Int'l Appl. | C12Q 1/02 |
| WO91/16429 | 10/1991 | PCT Int'l Appl. | C12N 15/12 |
| WO91/16456 | 10/1991 | PCT Int'l Appl. | C12Q 1/68 |
| WO92/05286 | 4/1992 | PCT Int'l Appl. | C12Q 1/68 |

OTHER PUBLICATIONS

Inoue et al. "DNA-binding proteins," *Proc. Natl. Acad. Sci. USA 86:* 3689-3693 (1989).

Lech, K. et al., "DNA-Bound Fos Protein Activate Transcription in Yeast," *Cell 52:*179-184 (1988).

Dang, C. V. et al., "Involvement of the 'leucine zipper' region in the pligomerization and transforming activity of human c-myc protein," *Nature 337:*664-666 (1989).

Dang, Chi V., "Detection and Use of Recombinant Staphylococcal Protein A Fusion Proteins to Localize Nucleic-Acid Domains of Proteins," *Analytical Biochem. 174:*313-317 (1988).

Prendergast, G. C. et al., "Methylation-Sensitive Sequence-Specific DNA Binding by the c-Myc Basic Region," *Science 251:186-189 (1991).*

Gregor, P. D. et al., "The adenovirus major late transcription factor USF is a member of the helix-loop-helix group of regulatory proteins and binds to DNA as a dimer," *Genes & Develop. 4:*1730-1740 (1990).

Blackwell, T. K. et al., "Differences and Similarities in DNA-Binding Preferences of MyoD and E2A Protein Complexes Revealed by Binding Site Selection," *Science 250:* 1104-1110 (1990).

Ludwig, S. R. et al., "Maize R Gene Family: Tissue-Specific Helix-Loop-Helix Proteins," *Cell 62:* 849-851 (1990).

Blackwood, E. M. et al., "Max: A Helix-Loop-Helix Zipper Protein That Forms a Sequence-Specific DNA-Binding Complex with Myc," *Science 251:* 1211-1217 (1991).

Kerkhoff, E. et al., "Myc protein structure: localization of DNA-binding and protein dimerization domains," *Oncogene 6:*93-102 (1991).

Turner, R. et al., "Leucine Repeats and an Adjacent DNA Binding Domain Mediate the Formation of Functional cFos-cJun Heterodimers," *Science 243:*1689-1694 (1989).

(List continued on next page.)

Primary Examiner—Robert J. Hill, Jr.
Assistant Examiner—John D. Ulm
Attorney, Agent, or Firm—Sterne, Kessler, Goldstein & Fox

[57] ABSTRACT

A rapid, simple and inexpensive method to screen and classify proteins as partners of dimeric proteins is described. The method utilizes fusion protein constructs containing a DNA binding domain and complementary dimerization domains from a different protein. According to the method of the invention, protein partner heterodimer formation is detected by the ability of the protein partner to displace formation of DNA binding domain homodimers, and thus reveal a phenotypic change in a bacterial host which was dependent upon maintenance of the DNA binding domain homodimer configuration. The method of the invention may further be used to identify compounds of interest which inhibit such heterodimer formation, and especially to identify compounds which prevent heterodimer formation and activation of oncogenic transcriptional regulatory proteins.

14 Claims, 2 Drawing Sheets

OTHER PUBLICATIONS

Kouzarides, T. et al., "The role of the leucine zipper in the fos-jun interaction," *Nature 336:*646-651 (1988).

Halazonetis, T. D. et al., "c-Jun Dimerizes with Itself and with c-Fos, Forming Complexes of Different DNA Binding Affinities," *Cell 55:*917-924 (1988).

Gentz, R. et al., "Parallel Association of Fos and Jun Leucine Zippers Juxtaposes DNA Binding Domains," *Science 243:*1695-1699 (1989).

Blackwell, T. K. et al., "Sequence-Specific DNA Binding by the c-Myc Protein," *Science 250:*1149-1151 (1990).

Lüscher, B. et al., "New Light on Myc and Myb. Part I. Myc," *Genes & Develop. 4:*2025-2035 (1990).

Science 235:305-311, 1987, Bishop, J. M. "The Molecular Genetics of Cancer".

Ann. Rev. of Genet. 20:361-384, 1986, Cole, M. D. "The oncogene: Its Role In Transformation and Differentiation".

Cell 42:23-38, 1985, Bishop, J. M. "Viral Oncogenes".

Nature 304:596-602, 1983, Land, H. et al. "Tumorgenet conversion of primary embryo fiboblasts requires at least #no cooperating oncogenes".

Genes Devl:1311-1326, 1987, Defino, R. A. et al. "The human Myc gene family:Structure and activity of L-myc and an L-myc pseutogene".

Cell 34:774-787, 1983, Dalley, R. A. et al. "The Human c-myc oncogene:Structural Consequences of Translocation into the FgH focus in Bu-hitt lymphoma".

Ah, Rev. Immun. 4:317-338, 1986, Kelly, K. et al. "The Regulation and Expression of c-myc in Normal and Malignant Cells".

Science 238:1337-1339, 1987, Vermus, H. E. "Oncogenes and Transcription Control".

Cell 41:3-5, 1985, Kingston, R. E. et al. "Transcription control by onogenes".

Ann. Rev. Biochem 58:744-839, 1984, Johnson, P. R. et al. "Eukeryotic Transcription/Regulatory proteins".

Nature 341:24-25, 1989, Abel, T. et al. "Action of Leucin-Zipper".

Cell 61:9-11, 1990, Jones, N. "Transcriptional Regulation by Dimerization" Two sides to an Indestuos Relationship.

Cell 56:777-783, 1989, Murre, C. et al., "A New DNA Binding and Dimerization Motif in immunoglobulin Enhancer Binding, daughterless, Myod and Myc Proteins".

Cell 58:537-544, 1989, Murre, C. et al., "Interactions between Heterologous Helix-loop-Here Proteins Cooperation Complexes that Borgl Spectrically to a Connol DNA Sequences".

P.N.A.S. 85:5834-5838, 1988, Hollos, M. et al., "A repression heterodimer binds to a chimeric operator".

Nature 341:392, 1989, Prendergast, C. C. et al. "Memory T Cells".

Science 247:467-470, 1990, Menthorn, P. et al. "Two Distinct Transcription Factors That Bind the Immunoglobulin Enhancer Me5/kE2 Motif".

Abstract, 8th Ann. Meeting on Oncogins, Frederick, M. D. 1989, Dist, "Analysis of c-Myc Binding to Enhance Motifs".

Nature 316:601-605, 1985, Wharton R. P. et al. "Charging the binding spestricity of larepresso-by redesigning an d-lextix".

EMBO J.1:541-595, 1982, Gicquet-Sanze et al. "Homology between different procarytor DNA binding regulatory proteins and between their sites of action".

|       |                                                      |       |
|-------|------------------------------------------------------|-------|
|       | AGGAGGAACAAGAAGATGA                                  | 5000  |
|       | luGluGluGlnGluAspGl                                  |       |
| 5001  | GGAAGAAATCGATGTTGTTTCTGTGGAAAAGAGGCAGGCTCCTGGCAAAA   | 5050  |
|       | uGluGluIleAspValValSerValGluLysArgGlnAlaProGlyLysA   |       |
| 5051  | GGTCAGAGTCTGGATCACCTTCTGCTGGAGGCCACAGGAAACCTCCTCAC   | 5100  |
|       | rgSerGluSerGlySerProSerAlaGlyGlyHisSerLysProProHis   |       |
| 5101  | AGCCCACTGGTCCTCAAGAGGTGCCACGTCTCCACACATCAGCACAACTA   | 5150  |
|       | SerProLeuValLeuLysArgCysHisValSerThrHisGlnHisAsnTy   |       |
| 5151  | CGCAGCGCCTCCCTCCACTCGGAAGGACTATCCTGCTGCCAAGAGGGTCA   | 5200  |
|       | rAlaAlaProProSerThrArgLysAspTyrProAlaAlaLysArgValL   |       |
| 5201  | AGTTGGACAGTGTCAGAGTCCTGAGACAGATCAGCAACAACCGAAAATGC   | 5250  |
|       | ysLeuAspSerValArgValLeuArgGlnIleSerAsnAsnArgLysCys   |       |
|       |                                            #2        |       |
| 5251  | ACCAGCCCCAGGTCCTCGGACACCGAGGAGAATGTCAAGAGGCGAACACA   | 5300  |
|       | ThrSerProArgSerSerAspThrGluGluAsnVal\|LysArgArgThrHi |       |
| 5301  | CAACGTCTTGGAGCGCCAGAGGAGGAACGAGCTAAAACGGAGCTTTTTTG   | 5350  |
|       | sAsnValLeuGluArgGlnArgArgAsnGluLeuLysArgSerPhePheA   |       |
|       |                                        H1            |       |
| 5351  | CCCTGCGTGACCAGATCCCGGAGTTGGAAAACAATGAAAAGGCCCCCAAG   | 5400  |
|       | laLeuArgAspGlnIleProGluLeuGluAsnAsnGluLysAlaProLys   |       |
| 5401  | GTAGTTATCCTTAAAAAAGCCACAGCATACATCCTGTCCGTCCAAGCAGA   | 5450  |
|       | ValVal IleLeuLysLysAlaThrAlaTyrIleLeuSerValGlnAlaGl  |       |
|       |            H2                          #10           |       |
| 5451  | GGAGCAAAAGCTCATTTCTGAAGAGGACTTGTTGCGGAAACGACGAGAAC   | 5500  |
|       | uGluGlnLysLeuIleSerGluGluAspLeuLeuArgLysArgArgGluG   |       |
| 5501  | AGTTGAAACACAAACTTGAACAGCTACGGAACTCTTGTGCGTAAGGAAAA   | 5550  |
|       | lnLeuLysHisLysLeuGluGlnLeuArgAsnSerCysAlaEnd         |       |
|       |                                          #9         |       |

FIG.1

```
5551  GTAAGGAAAACGATTCCTTCTAACAGAAATGTCCTGAGCAATCACCTATG  5600
5601  AACTTGTTTCAAATGCATGATCAAATGCAACCTCACAACCTTGGCTGAGT  5650
5651  CTTGAGACTGAAAGATTTAGCCATAATGTAAACTGCCTCAAATTGGACTT  5700
5701  TGGGCATAAAAGAACTTTTTTATGCTTACCATCTTTTTTTTTCTTTAAC  5750
5751  AGATTTGTATTTAAGAATTGTTTTTAAAAAATTTTAAGATTTACACAATG  5800
5801  TTTCTCTGTAAATATTGCCATTAAATGTAAATAACTTTAATAAAACGTTT  5850
5851  ATAGCAGTTACACAGAATTTCAATCCTAGTATATAGTACCTAGTATTATA  5900
5901  GGTACTATAAACCCTAATTTTTTTATTTAAGTACATTTGCTTTTTAAA    5950
5951  GTTGATTTTTTCTATTGTTTTAGAAAAAATAAAATAACTGGCAAATAT    6000
6001  ATCATTGAGCCAAATCTTAAGTTGTGAATGTTTTGTTTCGTTTCTTCCCC  6050
6051  CTCCCAACCACCACCATCCCTGTTTGTTTTCATCAATTGCCCCTTCAGAG  6100
6101  GGTGGTCTTAAGAAAGGCAAGAGTTTTCCTCTGTTGAAATGGGTCTGGGG  6150
6151  GCCTTAAGGTCTTTAAGTTCTTGGAGGTTCTAAGATGCTTCCTGGAGACT  6200
6201  ATGATAACAGCCGAAGTTGACAGTTAGAAGGAATGGCAGAAGGCAGGTGA  6250
6251  GAAGGTGAGAGGTAGGCAAAGGAGATACAAGAGGTCAAAGGTAGCAGTTA  6300
6301  AGTACACAAAGAGGCATAAGGACTGGGGAGTTGGGAGGAAGGTGAGGAAG  6350
6351  AAACTCCTGTTACTTTAGTTAACCAGTGCCAGTCCCCTGCTCACTCCAAA  6400
```

FIG.1 cont.

PROTEIN PARTNER SCREENING ASSAYS AND USES THEREOF

CROSS-REFERENCES TO RELATED APPLICATIONS

This application is a continuation-in-part of U.S. application No. 07/915,745 filed Jul. 21, 1992, now abandoned which is a continuation of U.S. application No. 07/815,880, filed Jan. 7, 1992 now abandoned which is a continuation of U.S. application No. 07/510,254 filed Apr. 19, 1990 now abandoned.

FIELD OF THE INVENTION

This invention is in the field of molecular biology and is directed to a method of identifying a peptide capable of associating with another peptide in a heterodimeric complex. The invention is also directed to a method of identifying inhibitors of such heterodimeric complex formation.

BACKGROUND OF THE INVENTION

Many regulatory proteins are heterodimers, that is, they are composed of two different peptide chains which interact to generate the native protein.

Among such regulatory proteins are DNA binding proteins which are capable of binding to specific DNA sequences and thereby regulating transcription of DNA into RNA. The dimerization of such proteins is necessary in order for these proteins to exhibit such binding specificity. A large number of transcriptional regulatory proteins have been identified: Myc, Fos, Jun, Ebp, Fra-1, Jun-B, Sp1, H2TF-1/NF-κB-like protein, PRDI, TDF, GLI, Evi-1, the glucocorticoid receptor, the estrogen receptor, the progesterone receptor, the thyroid hormone receptor (c-erbA) and ZIF/268, OTF-1(OCT1), OTF-2(OCT2) and PIT-1; the yeast proteins GCN4, GAL4, HAP1, ADR1, SWI5, ARGRII and LAC9, mating type factors MATα1, MATα2 and MATa1; the Neurospora proteins cys-3 and possibly cpc-1; and the Drosophila protein bsg 25D, kruppel, snail, hunchback, serendipity, and suppressor of hairy wing, antennapedia, ultrabithorax, paired, fushi tarazu, cut, and engrailed. Eukaryotic transcriptional regulatory proteins, and the methods used to characterize such proteins, have been recently reviewed (Pabo, C.O. et al., Ann. Rev. Blochem. 61:1053–1095 (1992); Johnson, P. F. et al., Ann. Rev. Blochem. 58:799–839 (1989)).

Members of the mammalian transcriptional regulatory protein families Jun/Fos and ATF/CREB only bind to DNA as dimers. The proteins in these families are "leucine zipper" proteins which contain a region rich in basic amino acids followed by a stretch of about 35 amino acids which contains 4–5 leucine residues separated from each other by 6 amino acids (the "leucine zipper" region). Collectively, the combination of a basic region and the leucine zipper region is termed the bZIP domain.

Generally, it is the basic region which has been found to be predominantly involved in contacting DNA whereas the zipper region mediates the dimerization. Many dimeric combinations are possible, however, the particular nature of the zipper specifies which partnerships are permissible (Abel, T. et al., Nature 341:24–25 (1989)).

Another large family of proteins contains the DNA binding/dimerization motif known as the basic helix-loop-helix motif (bHLH) (Jones, N., Cell 61:9–11 (1990)). A bHLH protein generally contains a basic N-terminus followed by a helix-loop-helix structure; two short amphipathic helices containing hydrophobic residues at every third or fourth position. The sequence of the basic region characteristically reveals no indication of an amphipathic helix. The intervening loop region usually contains one or more helix-breaking residues.

The bHLH motif was first detected in two proteins, E12 and E47, that bind to a specific "E box" DNA enhancer sequence found in immunoglobulin enhancers (Murre C. et al., Cell 56:777–783 (1989)). E motifs generally are double stranded variants of the 5'-CAGGTGGC-3'consensus sequence. For example, the μE1 motif is GTCAAGATGGC [Seq. ID NO. 1], μE2 motif is AGCAGCTGGC [SEQ ID NO. 2], μE3 is GTCATGTGGC [Seq. ID NO. 3], μE is TGCAGGTGT (Murre, C. et al., Cell 56:777–783 (1989)). Like many transcriptional factors, peptides containing the bHLH motif often dimerize with each other, either as a homodimer which contains two identical peptides or as a heterodimer which contains two different peptides. Examples of heterodimeric complex of two bHLH proteins binding DNA with a greater efficiency than homodimeric complexes of either peptide in the heterodimer are known (Murre C. et al., Cell 56:777–783 (1989); Murre, C et al., Cell 58:537–544 (1989)).

Identification of partners which direct protein-DNA binding and compounds which inhibit such activity by inhibiting such protein partner interaction could be very useful. For example, identification of partners of the myc protein and inhibitors of myc-partner interactions could provide a means for treating diseases in which expression and activity of myc is a factor in promoting cell growth or in maintaining the cell in a transformed state.

Myc is a bHLH protein and the bHLH domain of c-myc is encoded in c-myc amino acids 354–411. The sequence homology between the proteins expressed by the three myc genes (human N-myc 393–437, human c-myc 354–411, and human L-myc 289–338) and other genes which contain a bHLH domain have been compared (Murre C. et al., Cell 56:777–783 (1989)).

Proteins such as myc which contain the bHLH motif also possess the ability to dimerize with other bHLH motif proteins. Such interactions among bHLH proteins may play a critical role in their function and/or regulation. Identification of these protein partners would be useful not only in understanding how these proteins function, but also in developing or identifying inhibitors of these proteins. For example, identification of myc-partners would make it possible to identify inhibitors of myc-partner interactions. By inhibiting such interactions, inhibition and/or control of myc-induced cell growth may be achieved.

To date, no myc inhibitors have been identified. The identification of such inhibitors has suffered for lack of a simple, inexpensive and reliable screening assay which could rapidly identify potential inhibitors and active derivatives thereof. Thus a need still exists for rapid, economical screening assays which identify specific inhibitors of oncogene activity.

SUMMARY OF THE INVENTION

Recognizing the potential importance of inhibitors of oncoproteins in the therapeutic treatment of many forms of cancer, and cognizant of the lack of a simple assay system in which such inhibitors might be identified, the inventors have investigated the use of chimeric oncogene constructs in in vitro assays in prokaryotic hosts as a model system for identifying agents which alter oncogene expression.

These efforts have culminated in the development of a simple, inexpensive assay which can be used to identify protein partners in general, and partners of transcriptional regulatory proteins in particular.

The methods of the invention are especially useful for the identification of partners which influence transcriptional regulatory proteins, and especially oncoprotein activity.

The method of the invention further provides a method of identifying, isolating and characterizing inhibitors of such partner formation and especially inhibitors of oncoprotein activity.

The invention further provides a quick, reliable and accurate method for objectively classifying compounds, including human pharmaceuticals, as inhibitors of oncogene activity.

The invention further provides a method of identifying protein partners by their ability to disrupt λcI induced repression of phage promoters in bacterial hosts which express fusion proteins containing the cI DNA binding domain and a dimerization domain from a protein of interest. Proteins identified by this method are partners of the protein from which the dimerization domain was obtained. Protein partners thus identified are already in a cloned form, amenable to further characterization.

BRIEF DESCRIPTION OF THE DRAWINGS

FIG. 1 shows the DNA sequence (Seq. ID No. 4) and protein sequence (Seq. ID No. 5) of human c-myc exon 3 and the sites used to synthesize the HLH/LZ and HLH fragments of c-myc.

DESCRIPTION OF THE PREFERRED EMBODIMENTS

In the description that follows, a number of terms used in recombinant DNA technology are extensively utilized. In order to provide a clearer and more consistent understanding of the specification and claims, including the scope to be given such terms, the following definitions are provided in alphabetical order.

Bioactive Compound. The term "bioactive compound" is intended to refer to any compound which induces a measurable response in the assays of the invention.

Cloning vehicle. A "cloning vehicle" is any molecular entity which is capable of providing a nucleic acid sequence to a host cell for cloning purposes. Examples of cloning vehicles include plasmids or phage genomes. A plasmid which can replicate autonomously in the host cell is especially desired. Alternatively, a nucleic acid molecule which can insert into the host cell's chromosomal DNA is especially useful.

Cloning vehicles are often characterized by one or a small number of endonuclease recognition sites at which such DNA sequences may be cut in a determinable fashion without loss of an essential biological function of the vehicle, and into which DNA may be spliced in order to bring about its replication and cloning.

The cloning vehicle may further contain a marker suitable for use in the identification of cells transformed with the cloning vehicle. Markers, for example, are tetracycline resistance or ampicillin resistance. The word "vector" is sometimes used for "cloning vehicle."

Compound. The term "compound" is intended to refer to a chemical entity, whether in the solid, liquid, or gaseous phase. The term should be read to include synthetic compounds, natural products and macromolecular entities such as polypeptides, polynucleotides, or lipids, and also small entities such as neurotransmitters, ligands, hormones or elemental compounds.

Dimeric Protein. The term "dimeric protein" is intended to refer to a protein which contains two polypeptide chains that associate with one another, but which are not bound to one another by an amino acid linkage. Association of the polypeptide chains may be due to, for example, hydrogen bonding, ionic interactions, hydrophobic interactions, disulfide bonds, and the like.

Dimerization Domain. The term "dimerization domain" is intended to refer to that portion of each polypeptide chain of a dimeric protein which is necessary for the polypeptide chains to associate with one another. The dimerization domains of a dimeric protein, which may be identical or different, are referred to herein as complimentary to each other.

Expression. Expression is the process by which the information encoded within a gene is transcribed and translated into protein.

A nucleic acid molecule, such as a DNA or gene is said to be "capable of expressing" a polypeptide if the molecule contains the sequences which code for the polypeptide and the expression control sequences which, in the appropriate host environment, provide the ability to transcribe, process and translate the genetic information contained in the DNA into a protein product, and if such expression control sequences are operably-linked to the nucleotide sequence which encodes the polypeptide.

Expression vehicle. An "expression vehicle" is a vehicle or vector similar to a cloning vehicle but is especially designed to provide sequences capable of expressing the cloned gene after transformation into a host.

In an expression vehicle, the gene to be cloned is operably-linked to certain control sequences such as promoter sequences.

Expression control sequences will vary depending on whether the vector is designed to express the operably-linked gene in a prokaryotic or eukaryotic host and may additionally contain transcriptional host specific elements such as operator elements, upstream activator regions, enhancer elements, termination sequences, tissue-specificity elements, and/or translational initiation and termination sites.

Functional Derivative. A "functional derivative" of a fusion protein is a protein which possesses an ability to dimerize with a partner protein, and/or an ability to bind to a desired DNA target, that is substantially similar to the ability of the fusion protein constructs of the invention to dimerize. By "substantially similar" is meant that the above-described biological activities are qualitatively similar to the fusion proteins of the invention but quantitatively different. For example, a functional derivative of a fusion protein might recognize the same target as the fusion protein, or form heterodimers with the same partner protein, but not with the same affinity.

As used herein, for example, a peptide is said to be a "functional derivative" when it contains the amino acid sequence of the fusion protein plus additional chemical moieties not usually a part of a fusion protein. Such moieties may improve the derivative's solubility, absorption, biological half-life, etc. The moieties may alternatively decrease the toxicity of the derivative, or eliminate or attenuate any undesirable side effect of the derivative, etc. Moieties capable of mediating such effects are disclosed in *Remington's Pharmaceutical Sciences* (1980). Procedures for coupling such moieties to a molecule are well known in the art.

A functional derivative of a fusion protein may or may not contain post-translational modifications such as covalently linked carbohydrate, depending on the necessity of such modifications for the performance of the methods of the invention.

The term "functional derivative" is intended to encompass functional "fragments," "variants," "analogues," or "chemical derivatives" of a molecule.

Fusion protein. As used herein, "fusion protein" is a hybrid protein which has been constructed to contain domains from two different proteins.

The term "fusion protein gene" is meant to refer to a DNA sequence which codes for a fusion protein, including, where appropriate, the transcriptional and translational regulatory elements thereof.

Heterodimer. The term "heterodimer" or "heterodimeric protein" is intended to refer to a protein which contains two different polypeptide chains that associate with one another, but which are not bound to one another by an amino acid linkage.

Homodimer. The term "homodimer" or "homodimeric protein" is intended to refer to a protein which contains two identical polypeptide chains that associate with one another, but which are not bound to one another by an amino acid linkage. This term may be modified to refer only to a particular portion of a dimeric protein. For instance, a DNA binding domain homodimer is intended to refer to any dimeric protein containing identical DNA binding domains on its separate polypeptide chains.

Host. By "host" is meant any organism that is the recipient of a cloning or expression vehicle as defined herein. Appropriate hosts for use in the method of the invention include, but are not limited to, bacteria, yeast, and mammalian cells.

Marker Gene. The term "marker gene" is intended to refer to a gene whose expression in a host cell produces a readily observable, assayable, or selectable phenotype. Examples of marker genes which may be useful in the method of the invention include, but are not limited to, lacZ, aada (which confers spectinomycin and streptomycin resistance), and ble-1 (which confers bleomycin and phleomycin resistance).

Operably-linked. As used herein, two macromolecular elements are operably-linked when the two macromolecular elements are physically arranged such that factors which influence the activity of the first element cause the first element to induce an effect on the second element.

Promoter. A "promoter" is a DNA sequence located proximal to the start of transcription at the 5' end of the transcribed sequence, at which RNA polymerase binds or initiates transcription. The promoter may contain multiple regulatory elements that interact in modulating transcription of the operably-linked gene.

Protein Partner. The term "protein partner" is intended to refer to a polypeptide chain capable of associating with a heterologous polypeptide chain to form a heterodimeric protein. The two polypeptide chains of a heterodimeric protein are herein referred to as "partners" of one another. A polypeptide chain of a homodimeric protein may act as a partner in a heterodimeric protein.

Response. The term "response" is intended to refer to a change in any parameter which can be used to measure and describe the effect of a compound on the activity of a protein. The response may be revealed as a physical change (such as a change in phenotype) or a molecular change (such as a change in a reaction rate or affinity constant). Detection of the response may be performed by any means appropriate.

Variant. A "variant" of a fusion protein is a protein which contains an amino acid sequence that is substantially similar to, but not identical to, the amino acid sequence of a fusion protein constructed from naturally-occurring domains, that is, domains containing the native with the amino acid sequence.

By a "substantially similar" amino acid sequence is meant an amino acid sequence that is highly homologous to, but not identical to, the amino acid sequence found in a fusion protein. Highly homologous amino acid sequences include sequences of 80% or more homology, and possibly lower homology, especially if the homology is concentrated in domains of interest.

Transcription regulatory proteins, which normally function as dimeric proteins, have been found to possess discrete dimerization domains and DNA binding domains. The inventors have used these findings to develop the method of the invention for identifying a partner of a dimeric protein. This method involves construction of chimeric peptides with (1) known complementary dimerization domains and (2) DNA binding domains which, when present in homodimer form, are capable of conferring a detectable phenotype upon a host cell (preferably a bacterial host cell, such as *E. coli*). In the host cell, the chimeric peptides form DNA binding domain homodimers by association of the known complementary dimerization domains. Protein partners capable of associating with the chimeric peptides to form heterodimeric proteins will interfere with formation of the chimeric peptides into DNA binding domain homodimers. By monitoring the homodimer-conferred phenotype in the host cell, formation of interfering heterodimers may be detected and protein partners thus identified.

This method of the invention is generally useful to identify partners for any homodimer or heterodimer. For a homodimer, a single chimeric peptide containing the dimerization domain of the homodimer is used. For a heterodimer, two separate chimeric peptides are used; each containing one of the complementary dimerization domains of the heterodimer. The chimeric peptides also contain a DNA binding domain that confers a detectable phenotype in homodimer form.

DNA binding domains useful in construction of chimeric peptides of the invention may be obtained from proteins where they have been identified. For example, DNA binding domains may be obtained from bacteriophage repressors, such as bacteriophage lambda ($\lambda$) repressor. In particular, the lambda repressor protein cI is useful as a source of a DNA binding domain. cI represses lambda gene expression in its homodimeric form (Lambda II, Hendrix, R. W. et al., eds., Cold Spring Harbor Laboratory, New York, (1983).

Other DNA binding domains may be identified by a variety of techniques known in the art and previously used to identify such domains (see Pabo, C. O. et al., Ann. Rev. Biochem. 61:1053-1095 (1992); Johnson, P. E. et al., Annu. Rev. Biochem. 58:799-839 (1989) for a review of such domains).

DNA binding proteins, and DNA binding domains in such proteins, are identified and purified by their affinity for DNA. For example, DNA binding may be revealed in filter hybridization experiments in which the protein (usually labelled to facilitate detection) is allowed to bind to DNA immobilized on a filter or, vice versa, in which the DNA binding site (usually labelled) is bound to a filter upon which the protein has been immobilized. The sequence specificity and affinity of such binding is revealed with DNA protection assays and gel retardation assays. Purification of such proteins may be performed utilizing sequence-specific DNA affinity chromatography techniques, that is, column chromatography with a resin derivatized with the DNA to which the domain binds. Proteolytic degradation of DNA binding proteins may be used to reveal the domain which retains the DNA binding ability.

Dimeric proteins for which protein partners are desired to be identified serve as the source of dimerization domains useful in the construction of chimeric peptides of the invention. Dimerization domains may be currently known dimerization domains or those recognized by their homology to known dimerization domains. Other dimerization domains may be predicted by analysis of the three-dimensional structure of a protein using the amino acid sequence and computer analysis techniques commonly known in the art, for example, the Chou-Fasman algorithm. Such techniques allow for the identification of helical domains and other areas of interest, for example, hydrophobic or hydrophilic domains, in the peptide structure.

One class of known dimerization domains are the HLH domains, which share a common helix-loop-helix amino acid structure. The bHLH region of the c-myc protein is one such dimerization domain. This domain is complementary to itself and is therefore useful in the construction of chimeric peptides that form homodimers.

An HLH dimerization domain in a protein can be identified by comparison of an amino acid sequence with that of ten known HLH dimerization domains (amino acids 336-393 in E12, 336-393 in E47, 554-613 in daughterless, 357-407 in twist, 393-437 in human N-myc, 289-338 in human L-myc, 354-411 in human c-myc, 108-164 in MyoD, and genes of the achaete-scute locus: 101-167 of T4, 26-95 of T5 (Murre, C. et al., Cell 56:777-783 (1989)). The HLH dimerization domain contains two amphipathice helices separated by an intervening loop. The first helix contains 12 amino acids and the second helix contains 13 amino acids. Certain amino acids appear to be conserved in the HLH format, especially the hydrophobic residues which are present in the helices. Comparisons of the two sequences named above shows that there are five virtually identical hydrophilic residues within the 5' end of the homologous region and a set of mainly hydrophobic residues located in two short segments that are separated form one another by a sequence that generally contains prolines or clustered glycines.

Another class of known dimerization domains are the leucine zipper domains. This domain is typically about 35 amino acids long and contains a repeating heptad array of leucine residues and an exceedingly high density of oppositely charged amino acids (acidics and basics) juxtaposed in a manner suitable for intrahelical ion pairing. It is thought that the leucines extending from the helix of one polypeptide interdigitate with those of the analogous helix of a second peptide (the partner) and form the interlock termed the leucine zipper.

The DNA binding domain and the dimerization domain are engineered into the fusion protein in a manner which does not destroy the function of either domain; that is, the DNA binding domain, when properly dimerized, can recognize the DNA element to which it naturally binds and the dimerization domain retains the ability to dimerize with its partners. One of skill in the art, by running control assays, will be able to establish that the fusion protein functions in the proper manner.

The DNA sequence encoding the fusion protein may be chemically constructed or constructed by recombinant means known in the art. Methods of chemically synthesizing DNA are well known in the art (*Oligonucleotide Synthesis, A Practical Approach*, M. J. Gail, ed., IRL Press, Washington, D.C., 1094; *Synthesis and Applications of DNA and RNA*, S. A. Narang, ed., Academic Press, San Diego, Calif., 1987). Because the genetic code is degenerate, more than one codon may be used to construct the DNA sequence encoding a particular amino acid (Watson, J. D., In: *Molecular Biology of the Gene*, 3rd edition, W. A. Benjamin, Inc., Menlo Park, Calif., 1977, pp. 356-357).

To express the recombinant fusion constructs of the invention, transcriptional and translational signals recognizable by the host are necessary. A cloned fusion protein gene, obtained through the methods described above, and preferably in a double-stranded form, may be operably-linked to sequences controlling transcriptional expression in an expression vector, and introduced, for example by transformation, into a host cell to produce the recombinant fusion proteins, or functional derivatives thereof, for use in the methods of the invention.

Transcriptional initiation regulatory signals can be selected which allow for repression or activation of the expression of the gene encoding the fusion protein, so that expression of the fusion construct can be modulated, if desired. Of interest are regulatory signals which are temperature-sensitive so that by varying the temperature, expression can be repressed or initiated, or are subject to chemical regulation, for example, by a metabolite or a substrate added to the growth medium. Alternatively, the fusion construct may be constitutively expressed in the host cell.

It is necessary to express the proteins in a host wherein the ability of the protein to retain its biological function is not hindered. Expression of proteins in bacterial hosts is preferably achieved using prokaryotic regulatory signals.

Expression vectors typically contain discrete DNA elements such as, for example, (a) an origin of replication which allows for autonomous replication of the vector, or elements which promote insertion of the vector into the host's chromosome in a stable manner, and (b) specific genes which are capable of providing phenotypic selection in transformed cells. Many appropriate expression vector systems are commercially available which are useful in the methods of the invention.

Once the vector or DNA sequence containing the construct(s) is prepared for expression, the DNA construct(s) is introduced into an appropriate host cell by any of a variety of suitable means, for example by transformation. After the introduction of the vector, recipient cells are grown in a selective medium, which selects for the growth of vector-containing cells. Expression of the cloned gene sequence(s) results in the production of the fusion protein.

If the fusion protein DNA encoding sequence and an operably-linked promoter is introduced into a recipient host cell as a non-replicating DNA (or RNA) molecule, which may either be a linear molecule or, more preferably, a closed covalent circular molecule which is incapable of autonomous replication, the expression of the fusion protein may occur through the transient expression of the introduced sequence.

Genetically stable transformants may be constructed with vector systems, or transformation systems, whereby the fusion protein DNA is integrated into the host chromosome. Such integration may occur de novo within the cell or be assisted by transformation with a vector which functionally inserts itself into the host chromosome, for example, with bacteriophage, transposons or other DNA elements which promote integration of DNA sequences in chromosomes.

Cells which have been transformed with the fusion protein DNA vectors of the invention are selected by also introducing one or more markers which allow for selection of host cells which contain the vector. Markers incorporated in the vector may provide, for example, biocide resistance, e.g., resistance to antibiotics, or the like.

The transformed host cell can be fermented according to means known in the art to achieve optimal cell growth, and also to achieve optimal expression of the cloned fusion protein sequence fragments. Optimal expression of the fusion protein is expression which provides no more than the same moles of fusion protein subunit as the moles of the partner protein which are being expressed. However, variations in this amount are acceptable if they do not prevent the partner from forming heterodimers with the fusion protein, thereby interfering with fusion protein homodimer activity.

Any protein that possesses a binding domain which can form a heterodimer with the fusion protein will impair or prevent the formation of fusion protein homodimers. Such proteins can thus be identified by their ability to interfere with the phenotype conferred by the fusion protein homodimer.

In one embodiment the bacterial host, which is expressing a fusion protein as described above, is transformed with a λ expression library capable of expressing cloned eukaryotic genes. Those cells transformed with a eukaryotic gene expressing a protein which is a partner of the fusion protein can then be detected due to loss of the phenotype conferred by the fusion partner homodimer.

λgt11 packaging systems for the creation of expression libraries from mRNA, which are useful in the methods of the invention, are known in the art and may be obtained commercially (for example, through Promega Corporation, Madison, Wis.). Further, custom genomic expression libraries may also be obtained commercially. Using the commercial kits, an oligo(dT)-primed cDNA library in λgt11 may be generated with the use of cytoplasmic poly(A)-containing mRNA from any desired mammalian source. To induce expression of the cloned proteins contained therein, 10 mM IPTG (isopropyl-thiogalactoside) may be added.

A particular advantage of the method of the invention for the identification of protein partners is that, where approximately equal amounts of the fusion protein(s) and the protein partner are present in the host cell, the partner which is identified will have a higher affinity for the fusion protein(s) than the fusion protein(s) has to itself. If the disrupted dimerization is normally associated with a biological activity, such a protein partner is highly likely to be an important regulator of that biological activity. Further, the partner which is identified is already in a cloned, expressing form which may be utilized to obtain larger quantities of the protein for its isolation and further characterization by protein and molecular biology techniques known in the art.

Utilizing the above techniques, a chimeric peptide containing the bHLH dimerization region of c-myc and the DNA binding domain of cI was constructed (see Example 1). In the appropriate host cell, this chimeric peptide formed homodimers and repressed expression of the lacZ gene under the control of a lambda PL promoter and repressed phage lysis (see Example 2). Introduction of a partner protein into the host cell interfered with homodimer formation and de-repressed expression of the lacZ gene (see Example 3). The inventors used this method to screen a cDNA expression library and discovered a specific partner protein which associates with c-myc in vivo (see Example 3).

Compounds which inhibit the ability of protein partners to form interfering heterodimers, but which do not interfere with homodimer formation, may be identified by screening for the ability of a compound to reverse the interfering effect of the heterodimers and restore the homodimerconferred phenotype.

For example, for partners identified by de-repression of the lacZ gene as described above (see also Example X), compounds which prevent or otherwise interfere with heterodimer formation of the protein partners can be identified by screening for the ability of such compounds to restore repression of the lacZ gene and cause partner-containing cells to remain white when grown on X-gal plates. A compound which is found to restore lacZ gene repression in this example would be a compound which (a) prevents the fusion protein from associating with the partner peptide which is also being expressed in the host, (b) does not prevent homodimer formation and (e) does not inhibit cell growth.

The methods of the invention can be used to screen compounds in their pure form, at a variety of concentrations, and also in their impure form. The methods of the invention can also be used to identify the presence of such inhibitors in crude extracts, and to follow the purification of the inhibitors therefrom. The methods of the invention are also useful in the evaluation of the stability of the inhibitors identified as above, to evaluate the efficacy of various preparations.

Analogs of such compounds which are more permeable across bacterial host cell membranes may also be used. For example, dibutyryl derivatives often display an enhanced permeability.

Partners, and compounds which inhibit the association of such partners, of any type of transcriptional regulation protein which associates into dimers may be identified by the bacterial methods of the invention. The methods of the invention can also be used to identify partners, and compounds which interfere with such partners, of membrane-localized and/or cytoplasmicallylocalized proteins which associate into dimers.

It may be desired to further characterize the partner proteins of c-myc which are identified by the methods of the invention in a eukaryotic expression system. Such characterization may be performed according to the methods described in the inventor's copending U.S. patent application entitled "C-Myc Screening Assays," Ser. No. 07/785,567 filed Oct. 30, 1991 and incorporated herein by reference.

The following examples further describe the materials and methods used in carrying out the invention. The examples are not intended to limit the invention in any manner.

EXAMPLES

EXAMPLE 1

Construction of cI/c-myc Fusion Proteins

Chimeric genes capable of expressing fusion proteins containing the DNA binding domain of the lambda repressor cI and either 1) the c-myc basic helix-loop-helix (bHLH) dimerization domain or 2) the c-myc bHLH and leucine zipper (LZ) dimerization domains were constructed.

The promoter/operator region used consists of the β-lactamase promoter, lac operator and Shine-Delgarno (S.D.) sequence. The sequence is as follows:

```
GGA TCC TCT AAA TAC ATT CAA ATA AGT ATC CGC TCA TGA          [Seq. ID No. 6]
BamHI                          -35

GAC AAT AAC GGT AAC CAG AAT TGT GAG CGC TCA CAA TTT TG
    -10       BstEII

ATC GAT AGG AAA CTC GAG ATG...
ClaI    S.D.    XhoI   +1  cI
```

The N-terminal 336 bp (112 amino acids) of cI, which contains the DNA binding domain of this protein, was incorporated into this construct. This portion was amplified for cloning using polymerase chain reaction with primers adding XhoI and XbaI sites on the 5' and 3' ends, respectively. The promoter/operator and cI DNA were cloned into pUC18 digested with BamHI and XbaI to generate pUC3cI.

The sequence around the XbaI site is as follows:

```
5' CAG GCA GGG TCT AGA...              [SEQ ID NO. 7]
   Gln Ala Gly  XbaI
   cI coding seq.
```

The bHLH/LZ and bHLH fragments of c-myc were generated by PCR using a human c-myc cDNA as a template. The bHLH/LZ fragment used was a 258 bp fragment synthesized with primers starting at sites #2 and #9 (FIG. 1) with XbaI and SalI sites added at the 5' and 3' ends, respectively. The bHLH fragment used is a 165 bp fragment with XbaI and PstI sites added on the 5' and 3' ends, respectively. The boundaries of bHLH are at sites marked #2 and #10 (FIG. 1). The primer used at site #10 included a termination codon, as does that used at site #9. Insertion of the c-myc sequences into pU3cI was at the restriction sites corresponding to those added by the indicated PCR primers. The resulting constructs containing c-myc bHLH/LZ and bHLH were referred to as pU3.29 and pU3.210, respectively. As a result of the cloning procedure used, an XbaI site (TCT AGA) encoding amino acids Serine and Arginine was incorporated in-between the cI and c-myc sequences.

The chimeric cI/c-myc gene constructs in pUC18 were subcloned into pACYC177 (Chang, A. C. Y. et at., J. Bacteriol. 134:1141-1156 (1978)) as follows. Both chimeric genes were excised from pUC18 by digestion with HindIII, fill-in of the HindIII overlap with Klenow, and subsequent BamHI digestion. The chimeric gene fragments were then cloned into pACYC177 digested with BglI (filled in with Klenow) and BamHI. The resulting constructs were designated pYC188 which contains cI-bHLH/LZ and pYC192 which contains cI-bHLH. These pYC-construets confer kanamycin resistance upon transformed $E.\ coli$ host cells and are normally maintained in low copy number (5–20 copies/cell).

EXAMPLE 2

Assaying transformed bacteria for the phenotype conferred by the cI/c-myc fusion protein in homodimer form The DNA binding domain of the cI protein must be present in dimer form to function as a repressor of lambda transcription/infection. Native cI protein is unable to form dimers at physiological levels and is therefore functionally inactive. In contrast, fusion proteins containing a functional DNA binding domain from cI and a functional dimerization domain from c-myc should be able to form functional homodimer repressors. To detect the repressor phenotype in bacterial cells transformed with the cI/c-myc fusion constructs described in Example 1, two different assays were used.

In the "dot plaque assay" (DPA), transformed $E.\ coli$ cells were tested for susceptibility to lambda phage infection. These cells were predicted to be resistant to infection if the cI/c-myc fusion protein was adequately expressed and formed functional homodimers. Cell strains carrying fusion protein constructs were grown in L-broth media containing 30 μg/ml Kanamycin, 10 mM $MgSO_4$, and 0.2% maltose at 37° C. 0.25-0.5 ml of culture at an $OD_{600}$ of 1.0 to 2.0 was added to 3 mls of 48° C. top agar, mixed by vortexing and plated on prewarmed L-broth/Kanamycin plates. The top agar was allowed to solidify for 2-3 min. at room temperature and then 5 μl aliquots of lambda phage KH54 (provided by J. Hu and R. Sauer of the Massachussetts Institute of Technology) of titer $5 \times 10^1$–$5 \times 10^6$ plaque forming units (pfu) were dotted onto the top agar. Lambda phage KH4i[434] (provided by J. Hu and R. Sauer of the Massachussetts Institute of Technology), which carries the immunity region of phage 434 and is therefore not affected by lambda cI, was also dotted on as a control. Phage aliquots were allowed to dry and then the plates were incubated overnight at 37° C.

In this assay, the titer of phage required to create a dear spot is used as a measure of phage resistance. Bacteria that express native cI protein (which is unable to form dimers) from pACYC177 (Chang, A. C. Y. et al., J. Bacteriol. 134:1141-1156 (1978)) are not resistant and clearing can be seen at $<10^2$ pfu. In contrast, bacterial strains containing pYC188 and expressing the cI-bHLH/LZ fusion protein are resistant up to $10^5$–$10^6$ pfu and those containing pYC192 and expressing the cI-bHLH are resistant up to $10^7$ pfu. This resistance demonstrates the ability of the cI/c-myc fusion proteins to dimerize and effectively repress phage transcription/infection.

In the second assay, referred to herein as the X-gal assay, cells transformed with the cI/c-myc fusion construct pYC192 also contained a chimeric lacZ gene under the control of the lambda Pt, promoter. In these host cells, expression of functional cI/c-myc fusion protein would be expected to repress lacZ expression via repression of the lambda $P_L$ promoter. Expression of the lacZ gene is easily detectable by growth of cells on X-gal containing media. Cells expressing lacZ become blue on this media while nonexpressing or poorly expressing cells become white or pale blue, respectively.

As expected, those cells transformed with pYC192 grew as white or pale blue colonies due to repression of the $P_L$-lacZ gene while nontransformed cells grew as blue colonies due to expression of the $P_L$-lacZ gene.

EXAMPLE 3

Screening a cDNA expression library for protein partners able to form heterodimers with the cI/c-myc fusion protein Interference with dimerization by direct protein-protein interaction between the dimerization domain of the chimeric repressor and a cDNA-encoded protein is the basis for the screening system of the invention. Upon dimerization of a repressor monomer with a heterologous protein partner, which is not part of a cI fusion, the repressor chimera will be inactivated, as it is unable to bind DNA as a monomer.

The dot plaque assay (DPA) and X-gal assay, described in Example 2, were used in the screening system. Bacteria expressing cI/c-myc fusion proteins and exhibiting the homodimer conferred repression phenotype (either phage resistance or repression of $P_L$-lacZ expression) were used.

Screening with the Dot Plaque Assay

For the DPA, *E. coli* strain Y1090 (available from Promega Corporation, Madison, Wis.) expressing the chimetic repressor cI/c-myc, which are resistant to infection by λgt11, were used. Using this bacterial strain, λgt11 phage cDNA libraries, expressing cDNA encoded proteins as C-terminal fusions with lacZ, were screened. Only those phage containing a cDNA encoding a protein partner were predicted to form plaques due to interference with cI/c-myc repressor/homodimer formation.

λgt11 libraries were screened as follows. Bacterial strain Y1090 containing pYC192 and expressing cI-mycbHLH was grown in L-broth media containing Kanamycin, $Mg^{2+}$, and maltose essentially the same as for the DPA described in Example 2. 0.6 mls of culture were exposed to $1 \times 10^6$–$5 \times 10^6$ pfu of λgt11 library phage in liquid for 20 min. at 30° C. and then mixed with 7 mls of top agar and poured on 150 mm L-broth/Kanamycin plates. Plates were incubated overnight at 42° C. Four cDNA libraries were screened: one from HeLa cells, one from T cell line EIA, one from the pre-B cell line 38B9, and one from primary tonsil cells which are almost exclusively B cells. These libraries were respectively obtained from T. Kadesch at the University of Pennsylvania, K. Georgopolas of Massachussetts General Hospital, D. Weaver of the Dana Farber Cancer Institute (DFCI), and T. Tedder of DFCI.

The lambda cDNA libraries were also plated onto a bacterial strain expressing a chimeric repressor from plasmid PJH370 (Hu, J. C. et al., Science 250:1400–1403 (1990)) containing the c/DNA binding domain and the leucine zipper dimerization domain of the yeast transcription factor GCN4. For initial screenings, this strain acted as a comparison control to provide a baseline number of false positive plaques to be expected from the libraries resulting from phage mutations rendering them insensitive to the cI repressor. This strain also acted as a control for subsequent screening of putative positive plaques to determine if interference was due to a specific interaction with the cI/c-myc fusion protein or if the interference was of a more general nature, affecting the GCN4 dimerization domain as well.

For all libraries screened, essentially equal numbers of plaques were observed with the strain containing cI-GCN4 vs. the strain containing pYC192 (cI-myc), indicating that these plaques were likely to be false positives. The number of plaques obtained varied from 5 to approximately 250, depending on the library used. Ninety phage which formed plaques on the strain containing pYC192 were plaque purified and subsequently screened on the cI-GCN4 containing strain. All these phage again formed plaques, indicating that they did not specifically interact with the cI/c-myc fusion protein.

In light of these results, a subsequent experiment was performed to determine if a known protein partner could be detected with this screening procedure. In this experiment a bacterial strain expressing a cI/c-myc fusion protein was challenged with a λgt11 phage expressing a Max cDNA. Max is a bHLH/LZ protein known to interact with c-myc. The challenged cells exhibited full resistance to the Max λgt11 phage.

In contrast to these results, DPA screening for a predicted protein partner introduced before phage infection was successful. In this experiment, a pUC18 plasmid capable of expressing a protein containing the bHLH/LZ domains of c-myc, but not the DNA binding domain of cI, was introduced into a bacterial strain which already contained a pACYC177 plasmid capable of expressing a cI/c-myc fusion protein. The protein containing the bHLH/LZ domains was predicted to function as a partner to the cI/c-myc fusion protein and interfere with the repression of phage infection. As predicted, cells expressing cI/c-myc and the bHLH/LZ protein were approximately 100-fold less resistant to phage infection than cells expressing cI/c-myc only, as measured by the DPA.

These results indicate that the DPA can be used to screen for protein partners, but that the protein partner must be expressed in the bacteria before it is challenged with phage. Simultaneous introduction of the protein partner gene with the challenging phage, as occurs in the direct screen, probably does not work because the phage is effectively repressed before the protein partner gene is given a chance to express and interfere with the cI/c-myc fusion protein repressor.

Screening with the X-Gal Assay

As described above, in cells with an active cI/c-myc repressor the $P_L$-lacZ gene is turned off resulting in the generation of white colonies on X-gal indicator plates. Interference with repressor dimerization is predicted to yield blue colonies as the lacZ gene would be expressed (de-repressed).

Screening using the X-gal assay was performed as follows. The strain Y1090 was transformed with the lacZ target plasmid pNNP$_L$387 and pYC188 which expresses cI-bHLH/LZ. The plasmid pNNP$_L$387 was constructed by inserting a PCR generated DNA fragment containing the left promoter of phage lambda upstream of lacZ in pNN387 (provided by S. Elledge, Baylor University, See Elledge, S. J. et at., Genes & Develop. 3: 185–197 (1989)). These cells, when plated on L-broth/Kanamycin/Chloramphenicol/X-gal, form white to pale blue colonies. This strain, referred to as 10B18, was made competent for electroporation (see Current Protocols in Molecular Biology, sec. 1.8.4, Wiley Interscience, ed. by Ausubel et aL (1987)) and transformed with a plasmid-based cDNA library made from human peripheral blood lymphocytes which had been transformed with Epstein-Barr Virus (provided by S. Elledge, See Elledge, S. J. et at., Proc. Natl. Acad. Sci. USA 88: 1731–1735 (1991)). There were about $10^7$ recombinants in this once-amplified library.

10B18 was electroporated on two separate occasions with 500 ng of library DNA. Cells were allowed to recover from electroporation for 45 min. at 37° C. in SOC media and then plated on M9/0.2% mannitol with Chloramphenicol (20 $\mu$g/ml), Kanamycin (30 $\mu$g/ml), IPTG (2 mM), Ampicillin (50 $\mu$g/ml), and X-gal (0.004 %). The electroporations yielded $2.8 \times 10^6$ and $5.6 \times 10^5$ transformants, of which approximately 500 and 29, respectively, were blue. A total of 322 blue colonies were picked and restreaked to isolate single colonies. From these, 97 blue clonal colonies were isolated and plasmid DNAs were prepared. Plasmid DNA from each clone was then retransformed into 10B18 and plated as above. Only one clone consistently produced blue colonies.

This clone was shown to be specific for c-myc by comparing the phenotypes it produced in different repressor chimera backgrounds. Bacterial strains similar to 10B 18 which contain different cI-dimerization domain fusion constructs were used. These stains express cI fusions with the c-myc bHLH domain (10B19), the transcription factor E2/5bHLH domain (10BE2/5), or thyroid hormone receptor $\beta$ (10B$\beta$). The positive clone isolated in the original screen produced blue colonies only in 10B18 and 10B19, where dimerization was mediated by a c-myc domain. Strains 10BE2/5 and 10B$\beta$ remained white on X-gal plates after transformation with this clone.

The high number of false positives obtained during the initial rounds of screening could be due to the instability of the plasmid containing the chimeric repressor gene in the screening strain. Alternatively, blue colonies could result from an increase in the copy number of the P$_L$-lacZ containing plasmid or increased expression of the P$_L$-lacZ gene which titrates out repressor dimers. Whatever the cause, repeated passages through the 10B18 strain was effective in screening out false positives.

EXAMPLE 4

Identification of compounds which prevent c-myc partner formation

To identify compounds which inhibit c-myc partner heterodimerization without interfering with c-myc homodimerization, cells identified according to the method described in Example 3 which contain the cI/c-myc fusion protein and a partner protein are used along with cells containing only the cI/c-myc fusion protein as described in Example 2. These cells are further exposed to experimental compounds W, X, Y, and Z and the effect of such compounds on the homodimer/heterodimer dependent phenotype is determined.

Typical results from such an experiment are shown in Table 1.

TABLE 1

Identification of C-myc-protein Partner Inhibitors

| Compound | Protein Partner | Assay Phenotype |
|---|---|---|
| none | − | no plaques/white |
|  | + | plaques/blue |
| W | − | no plaques/white |
|  | + | plaques/blue |
| X | − | plaques/blue |
|  | + | plaques/blue |
| Y | − | no plaques/white |
|  | + | no plaques/white |

The results of the above table indicate that, in the absence of the partner protein, compound W had no effect on the ability of the cI/c-myc protein to form homodimers and exhibit the corresponding phenotype. Compound W also had no effect on the ability of the partner to form heterodimers with the myc fusion protein and reverse the homodimerconferred phenotype. Therefore, compound W will not be a compound of interest.

Compound X interfered with homodimer formation and therefore will not be a compound of interest.

Compound Y is an inhibitor of heterodimer formation. Compound Y did not interfere with homodimer formation but did interfere with heterodimer formation. Therefore, compound Y is a compound of interest as it may disrupt c-myc action in vivo.

All references cited herein are fully incorporated by reference. Having now fully described the invention, it will be understood by those with skill in the art that the scope may be performed within a wide and equivalent range of conditions, parameters and the like, without affecting the spirit or scope of the invention or any embodiment thereof.

---

What is claimed is:

1. A method for identifying and classifying a protein partner wherein said method comprises:
   (a) transformation of a host cell with a genetic construct capable of expressing a fusion protein, wherein said fusion protein contains a DNA binding domain and a dimerization domain complementary to itself which is not naturally associated with said DNA binding domain, and wherein said fusion protein forms a homodimer which confers a detectable phenotype upon said host cell;
   (b) transformation of said host cell of pan (a) with a genetic construct capable of expressing said protein partner;
   (c) culturing said host cell of pan (b) under conditions which express said fusion protein and said protein partner, said protein partner being expressed at levels equivalent to or greater than said fusion protein;
   (d) determining whether the phenotype conferred by said fusion protein of part (a) is present in said host cell of part (c); and
   (e) classifying said protein partner on the basis of the presence or absence of said phenotype.

2. A method of identifying and classifying a compound as an inhibitor of a protein partner, wherein said method comprises:
   (a) transformation of a bacterial host cell with a genetic construct capable of expressing a fusion protein, wherein said fusion protein contains a DNA binding domain and a dimerization domain complementary to itself which is not naturally associated with said DNA binding domain, and wherein said fusion protein forms a homodimer which confers a detectable phenotype upon said host cell;
   (b) transformation of said host cell of part (a) with a genetic construct capable of expressing said protein partner;
   (c) culturing said host cell of part (b) in the presence of said compound and under conditions which express said fusion protein and said protein partner, said protein partner being expressed at levels equivalent to or greater than said fusion protein;
   (d) determining the ability of said compound to prevent proteinpartner-induced interference of the phenotype conferred by said fusion protein of part (a); and
   (e) classifying said compound as an inhibitor of protein partner formation on the basis of the presence or absence of said phenotype.

3. The method of any one of claims 1 or 2, wherein said phenotype conferred by said fusion protein in homodimer form is the repression of expression of an assayable marker gene.

4. The method of claim 3, wherein said assayable marker is under the transcriptional control of the bacteriophage λ PL promoter.

5. The method of claim 4, wherein said assayable marker is the lacZ gene.

6. The method of any one of claims 1 or 2, wherein said DNA binding domain of said fusion protein is the DNA binding domain of bacteriophage λ cI repressor protein.

7. The method of claim 6, wherein said DNA binding domain of said cI repressor protein is the N-terminal 112 amino acids of said repressor protein.

8. The method of any one of claims 1 or 2, wherein said dimerization domain is a bHLH domain.

9. The method of claim 8, wherein said bHLH domain is from myc.

10. The method of claim 9, wherein said myc is c-myc.

11. The method of claim 10, wherein said bHLH domain is the amino acid sequence bounded by site numbers 2 and 10 of FIG. 1 of c-myc.

12. The method of any one of claims 1 or 2, wherein said dimerization domain is a bZIP domain.

13. A method for identifying and classifying a protein partner wherein said method comprises:
   (a) transformation of a bacterial host cell with a genetic construct capable of expressing a first fusion protein and a second fusion protein, wherein said first fusion protein contains a DNA binding domain and a first dimerization domain not naturally associated with said DNA binding domain, and wherein said second fusion protein contains said DNA binding domain and a second dimerization domain complementary to said first dimerization domain wherein said second dimerization domain is not naturally associated with said DNA binding domain, and wherein said first fusion protein and said second fusion protein form a DNA binding domain homodimer which confers a detectable phenotype upon said host cell;
   (b) transformation of said host cell of part (a) with a genetic construct capable of expressing said protein partner;
   (c) culturing said host cell of part (b) under conditions which express said first fusion protein, said second fusion protein, and said protein partner, said protein partner being expressed at levels equivalent to or greater than either said first fusion protein or said second fusion protein;

(d) determining whether the phenotype conferred by said DNA binding domain homodimer of part (a) is present in said host cell of part (c); and (e) classifying said protein partner on the basis of the presence or absence of said phenotype.

14. A method of identifying and classifying a compound as an inhibitor of a protein partner, wherein said method comprises:

(a) transformation of a bacterial host cell with a genetic construct capable of expressing a first fusion protein and a second fusion protein, wherein said first fusion protein contains a DNA binding domain and a first dimerization domain not naturally associated with said DNA binding domain, and wherein said second fusion protein contains said DNA binding domain and a second dimerization domain complementary to said first dimerization domain wherein said second dimerization domain is not naturally associated with said, and wherein said first fusion protein and said second fusion protein form a DNA binding domain homodimer which confers a detectable phenotype upon said host cell;

(b) transformation of said host cell of part (a) with a genetic construct capable of expressing said protein partner;

(c) culturing said host cell of part (b) in the presence of said compound and under conditions which express said first fusion protein, said second fusion protein, and said protein partner, said protein partner being expressed at levels equivalent to or greater than either said first fusion protein or said second fusion protein;

(d) determining the ability of said compound to prevent proteinpartner-induced interference of the phenotype conferred by said DNA binding domain homodimer of part (a); and (e) classifying said compound as an inhibitor of protein partner formation on the basis of the presence or absence of said phenotype.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 11 base pairs
        ( B ) TYPE: nucleic acid ( C ) STRANDEDNESS: double
            ( D ) TOPOLOGY: linear ( i i ) MOLECULE TYPE: DNA ( x i ) SEQUENCE DESCRIPTION: SEQ ID NO:1:

GTCAAGATGG C                                                                                        11

( 2 ) INFORMATION FOR SEQ ID NO:2:

( i ) SEQUENCE CHARACTERISTICS:
            ( A ) LENGTH: 10 base pairs
            ( B ) TYPE: nucleic acid
            ( C ) STRANDEDNESS: double
            ( D ) TOPOLOGY: linear ( i i ) MOLECULE TYPE: DNA ( x i ) SEQUENCE DESCRIPTION: SEQ ID NO:2:

AGCAGCTGGC                                                                                          10

( 2 ) INFORMATION FOR SEQ ID NO:3:

( i ) SEQUENCE CHARACTERISTICS:
            ( A ) LENGTH: 10 base pairs
            ( B ) TYPE: nucleic acid
            ( C ) STRANDEDNESS: double
            ( D ) TOPOLOGY: linear ( i i ) MOLECULE TYPE: DNA ( x i ) SEQUENCE DESCRIPTION: SEQ ID NO:3:

GTCATGTGGC                                                                                          10

( 2 ) INFORMATION FOR SEQ ID NO:4:

( i ) SEQUENCE CHARACTERISTICS:
            ( A ) LENGTH: 1419 base pairs
            ( B ) TYPE: nucleic acid
            ( C ) STRANDEDNESS: double
            ( D ) TOPOLOGY: linear ( i i ) MOLECULE TYPE: DNA ( x i ) SEQUENCE DESCRIPTION: SEQ ID NO:4:

AGGAGGAACA  AGAAGATGAG  GAAGAAATCG  ATGTTGTTTC  TGTGGAAAAG  AGGCAGGCTC        60

CTGGCAAAAG  GTCAGAGTCT  GGATCACCTT  CTGCTGGAGG  CCACAGGAAA  CCTCCTCACA       120

GCCCACTGGT  CCTCAAGAGG  TGCCACGTCT  CCACACATCA  GCACAACTAC  GCAGCGCCTC       180

CCTCCACTCG  GAAGGACTAT  CCTGCTGCCA  AGAGGGTCAA  GTTGGACAGT  GTCAGAGTCC       240

TGAGACAGAT  CAGCAACAAC  CGAAAATGCA  CCAGCCCCAG  GTCCTCGGAC  ACCGAGGAGA       300

ATGTCAAGAG  GCGAACACAC  AACGTCTTGG  AGCGCCAGAG  GAGGAACGAG  CTAAAACGGA       360

GCTTTTTTGC  CCTGCGTGAC  CAGATCCCGG  AGTTGGAAAA  CAATGAAAAG  GCCCCCAAGG       420

TAGTTATCCT  TAAAAAAGCC  ACAGCATACA  TCCTGTCCGT  CCAAGCAGAG  GAGCAAAAGC       480

TCATTTCTGA  AGAGGACTTG  TTGCGGAAAC  GACGAGAACA  GTTGAAACAC  AAACTTGAAC       540

AGCTACGGAA  CTCTTGTGCG  TAAGGAAAAG  TAAGGAAAAC  GATTCCTTCT  AACAGAAATG       600

TCCTGAGCAA  TCACCTATGA  ACTTGTTTCA  AATGCATGAT  CAAATGCAAC  CTCACAACCT       660

TGGCTGAGTC  TTGAGACTGA  AAGATTTAGC  CATAATGTAA  ACTGCCTCAA  ATTGGACTTT       720

GGGCATAAAA  GAACTTTTTT  ATGCTTACCA  TCTTTTTTTT  TTCTTTAACA  GATTTGTATT       780

TAAGAATTGT  TTTTAAAAAA  TTTTAAGATT  TACACAATGT  TTCTCTGTAA  ATATTGCCAT       840

TAAATGTAAA  TAACTTTAAT  AAAACGTTTA  TAGCAGTTAC  ACAGAATTTC  AATCCTAGTA       900

```
TATAGTACCT    AGTATTATAG    GTACTATAAA    CCCTAATTTT    TTTTATTTAA    GTACATTTTG         960

CTTTTTAAAG    TTGATTTTTT    TCTATTGTTT    TTAGAAAAAA    TAAAATAACT    GGCAAATATA        1020

TCATTGAGCC    AAATCTTAAG    TTGTGAATGT    TTTGTTTCGT    TTCTTCCCCC    TCCCAACCAC        1080

CACCATCCCT    GTTTGTTTTC    ATCAATTGCC    CCTTCAGAGG    GTGGTCTTAA    GAAAGGCAAG        1140

AGTTTTCCTC    TGTTGAAATG    GGTCTGGGGG    CCTTAAGGTC    TTTAAGTTCT    TGGAGGTTCT        1200

AAGATGCTTC    CTGGAGACTA    TGATAACAGC    CGAAGTTGAC    AGTTAGAAGG    AATGGCAGAA        1260

GGCAGGTGAG    AAGGTGAGAG    GTAGGCAAAG    GAGATACAAG    AGGTCAAAGG    TAGCAGTTAA        1320

GTACACAAAG    AGGCATAAGG    ACTGGGGAGT    TGGGAGGAAG    GTGAGGAAGA    AACTCCTGTT        1380

ACTTTAGTTA    ACCAGTGCCA    GTCCCTGCT     CACTCCAAA                                    1419
```

( 2 ) INFORMATION FOR SEQ ID NO:5:

( i ) SEQUENCE CHARACTERISTICS:
        ( A ) LENGTH: 186 amino acids
        ( B ) TYPE: amino acid
        ( D ) TOPOLOGY: both ( i i ) MOLECULE TYPE: protein ( x i ) SEQUENCE DESCRIPTION: SEQ ID NO:5:

```
Glu  Glu  Gln  Glu  Asp  Glu  Glu  Glu  Ile  Asp  Val  Val  Ser  Val  Glu  Lys
 1              5                        10                         15

Arg  Gln  Ala  Pro  Gly  Lys  Arg  Ser  Glu  Ser  Gly  Ser  Pro  Ser  Ala  Gly
               20                        25                   30

Gly  His  Ser  Lys  Pro  Pro  His  Ser  Pro  Leu  Val  Leu  Lys  Arg  Cys  His
          35                        40                        45

Val  Ser  Thr  His  Gln  His  Asn  Tyr  Ala  Ala  Pro  Pro  Ser  Thr  Arg  Lys
     50                        55                        60

Asp  Tyr  Pro  Ala  Ala  Lys  Arg  Val  Lys  Leu  Asp  Ser  Val  Arg  Val  Leu
65                        70                   75                         80

Arg  Gln  Ile  Ser  Asn  Asn  Arg  Lys  Cys  Thr  Ser  Pro  Arg  Ser  Ser  Asp
                    85                        90                   95

Thr  Glu  Glu  Asn  Val  Lys  Arg  Arg  Thr  His  Asn  Val  Leu  Glu  Arg  Gln
               100                       105                      110

Arg  Arg  Asn  Glu  Leu  Lys  Arg  Ser  Phe  Phe  Ala  Leu  Arg  Asp  Gln  Ile
          115                       120                      125

Pro  Glu  Leu  Glu  Asn  Asn  Glu  Lys  Ala  Pro  Lys  Val  Val  Ile  Leu  Lys
     130                       135                      140

Lys  Ala  Thr  Ala  Tyr  Ile  Leu  Ser  Val  Gln  Ala  Glu  Glu  Gln  Lys  Leu
145                       150                      155                      160

Ile  Ser  Glu  Glu  Asp  Leu  Leu  Arg  Lys  Arg  Arg  Glu  Gln  Leu  Lys  His
                    165                       170                      175

Lys  Leu  Glu  Gln  Leu  Arg  Asn  Ser  Cys  Ala
                    180                       185
```

( 2 ) INFORMATION FOR SEQ ID NO:6:

( i ) SEQUENCE CHARACTERISTICS:
        ( A ) LENGTH: 101 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:6:

```
GGATCCTCTA    AATACATTCA    AATAAGTATC    CGCTCATGAG    ACAATAACGG    TAACCAGAAT         60

TGTGAGCGCT    CACAATTTTG    ATCGATAGGA    AACTCGAGAT    G                              101
```

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:7:

CAGGCAGGGT CTAGA                    15